US007148026B2

(12) United States Patent
Tan

(10) Patent No.: US 7,148,026 B2
(45) Date of Patent: Dec. 12, 2006

(54) DOG MELANIN-CONCENTRATING HORMONE RECEPTOR

(75) Inventor: Carina Tan, Metuchen, NJ (US)

(73) Assignee: Merck & Co., Inc., Rahway, NJ (US)

( * ) Notice: Subject to any disclaimer, the term of this patent is extended or adjusted under 35 U.S.C. 154(b) by 717 days.

(21) Appl. No.: 10/333,379

(22) PCT Filed: Jul. 17, 2001

(86) PCT No.: PCT/US01/22458

§ 371 (c)(1),
(2), (4) Date: Jan. 17, 2003

(87) PCT Pub. No.: WO02/08290

PCT Pub. Date: Jan. 31, 2002

(65) Prior Publication Data

US 2003/0212252 A1    Nov. 13, 2003

Related U.S. Application Data

(60) Provisional application No. 60/219,669, filed on Jul. 21, 2000.

(51) Int. Cl.
*G01N 33/53* (2006.01)
*C07K 14/72* (2006.01)
*C12N 5/10* (2006.01)
*C12N 15/12* (2006.01)

(52) U.S. Cl. .................. 435/7.2; 530/350; 530/300; 536/23.5; 536/23.1; 435/69.1; 435/320.1; 435/325; 435/252.3; 435/254.11

(58) Field of Classification Search ............... None
See application file for complete search history.

(56) References Cited

U.S. PATENT DOCUMENTS

| 5,264,565 | A | 11/1993 | England et al. |
| 6,033,872 | A | 3/2000 | Bergsma et al. |
| 6,221,613 | B1 | 4/2001 | Salon et al. |
| 6,362,326 | B1 | 3/2002 | Sathe et al. |

FOREIGN PATENT DOCUMENTS

| WO | WO 96/18651 | 6/1996 |
| WO | WO 97/05252 | 2/1997 |
| WO | WO 99/28429 | 6/1999 |
| WO | WO 99/28492 | 6/1999 |
| WO | WO 00/37113 | 6/2000 |
| WO | WO 00/75166 | 12/2000 |
| WO | WO 01/05947 | 1/2001 |

OTHER PUBLICATIONS

Macdonald et al., Molecular characterization of the melanin-concentrating hormone/receptor complex: Identification of critical residues involved in binding and activation, Mol. Pharm. 58(1):217-225, Jul. 2000.*

Strader et al., Structural basis of Beta-adrenergic receptor function, FASEB J. 3:1825-1832, May 1989.*
Bonaldo et al., Normalization and subtraction:tow approaches to faciliate gene discovery, Genome Res. 6(9),791-806,1996.*
An, S. et al. "Identification and characterization of a melanin-concentrating hormone receptor", PNAS, 2001, vol. 98, pp. 7576-7581.
Bachner, D. et al. "Identification of melanin concentrating hormone (MCH) as the natural ligand for the orphan somatostatin-like receptor 1 (SLC-1)", FEBS Letters, 1999, vol. 457, pp. 522-524.
Brenton, C. et al. "Isolation and characterization of the human melanin-concentrating hormone gene and a variant gene", Molecular Brain Research, 1993, vol. 18, pp. 297-310.
Chambers, J. et al. "Melanin-concentrating hormone is the cognate ligand for the orphan G-protein-coupled receptor SLC-1", Nature, 1999, vol. 400, pp. 261-265.
Flier, J. et al. "Obesity and the Hypothalamus: Novel Peptides for New Pathways", Cell, 1998, vol. 92, pp. 437-440.
Hill, J. et al. "Molecular Cloning and Functional Characterization of MCH2, a Novel Human MCH Receptor", The Journal of Biological Chemistry, 2001, vol. 276, pp. 20125-20129.
Knigge, K. et al. "Melanotropic Peptides in the Mammalian Brain: The Melanin-Concentrating Hormone", Peptides, 1996, vol. 17, pp. 1063-1073.
Lembo, P. et al. "The receptor for the orexigenic peptide melanin-concentrating hormone is a G-protein-coupled receptor", Nature Cell Biology, 1999, vol. 1, pp. 267-271.
Mori, M. et al. "Cloning of a Novel G Protein-Coupled Receptor, SLT, a Subtype of the Melanin-Concentrating Hormone Receptor", Biochemical and Biophysical Research Communications, 2001, vol. 283, pp. 1013-1018.
Nahon, J. "The Melanin-Concentrating Hormone: From the Peptide to the Gene", Critical Reviews in Neurobiology, 1994, vol. 8, pp. 221-262.
Qu, D. et al. "A role for melanin-concentrating hormone in the central regulation of feeding behaviour", Nature, 1996, vol. 380, pp. 243-247.
Sailer, A. et al. "Identification and characterization of a second melanin-concentrating hormone receptor, MCH-2R", PNAS, 2001, vol. 98, pp. 7564-7569.
Saito, Y. et al. "Molecular characterization of the melanin-concentrating-hormone receptor", Nature, 1999, vol. 400, pp. 265-269.
Shimada, M. et al. "Mice lacking melanin-concentrating hormone are hypophagic and lean", Nature, 1998, vol. 396, pp. 670-674.
Shimomura, Y. et al. "Isolation and Identification of Melanin-Concentrating Hormone as the Endogenous Ligand of the SLC-1 Receptor", Biochemical and Biophysical Research Communications, 1999, vol. 261, pp. 622-626.

* cited by examiner

*Primary Examiner*—Lorraine Spector
*Assistant Examiner*—Claire M. Kaufman
(74) *Attorney, Agent, or Firm*—Jack L. Tribble; Sheldon O. Heber

(57) ABSTRACT

The present invention features polypeptides and nucleic acids related to a dog MCH receptor and uses of such polypeptides and nucleic acids. The dog MCH receptor is a G protein coupled receptor whose activity is stimulated by MCH binding.

16 Claims, 4 Drawing Sheets

|          | 1          |            |            |            | 50         |
|----------|------------|------------|------------|------------|------------|
| huMCH1R  | MDLEASLLPT | GPNASNTSDG | PDNLTSAGSP | PRTGSISYIN | IIMPSVFGTI |
| dogMCH1R | MDLEASLLPP | GPNASNTSEG | PDNLTSAGPP | RRTGNVSYIN | IIMPSVFGTI |
| ratMCH1R | MDLQTSLLST | GPNASNISDG | QDNLTLPGSP | PRTGSVSYIN | IIMPSVFGTI |

|          | 51         |            |            |            | 100        |
|----------|------------|------------|------------|------------|------------|
| huMCH1R  | CLLGIIGNST | VIFAVVKKSK | LHWCNNVPDI | FIINLSVVDL | LFLLGMPFMI |
| dogMCH1R | CLLGIIGNST | VIFAVVKKSK | LHWCSNVPDI | FIINLSVVDL | LFLLGMPFMI |
| ratMCH1R | CLLGIVGNST | VIFAVVKKSK | LHWCSNVPDI | FIINLSVVDL | LFLLGMPFMI |

|          | 101        |            |            |            | 150        |
|----------|------------|------------|------------|------------|------------|
| huMCH1R  | HQLMGNGVWH | FGETMCTLIT | AMDANSQFTS | TYILTAMAID | RYLATVHPIS |
| dogMCH1R | HQLMGNGVWH | FGETMCTLIT | AMDANSQFTS | TYILTAMAID | RYLATVHPIS |
| ratMCH1R | HQLMGNGVWH | FGETMCTLIT | AMDANSQFTS | TYILTAMTID | RYLATVHPIS |

|          | 151        |            |            |            | 200        |
|----------|------------|------------|------------|------------|------------|
| huMCH1R  | STKFRKPSVA | TLVICLLWAL | SFISITPVWL | YARLIPFPGG | AVGCGIRLPN |
| dogMCH1R | STKFRKPSVA | TLVICLLWAL | SFISITPVWL | YARLIPFPGG | TVGCGIRLPN |
| ratMCH1R | STKFRKPSMA | TLVICLLWAL | SFISITPVWL | YARLIPFPGG | AVGCGIRLPN |

|          | 201        |            |            |            | 250        |
|----------|------------|------------|------------|------------|------------|
| huMCH1R  | PDTDLYWFTL | YQFFLAFALP | FVVITAAYVR | ILQRMTSSVA | PASQRSIRLR |
| dogMCH1R | PDTDLYWFTL | YQFFLAFALP | FVVITAAYVR | ILQRMMSSVA | PASQRSIRLR |
| ratMCH1R | PDTDLYWFTL | YQFFLAFALP | FVVITAAYVK | ILQRMTSSVA | PASQRSIRLR |

|          | 251        |            |            |            | 300        |
|----------|------------|------------|------------|------------|------------|
| huMCH1R  | TKRVTRTAIA | ICLVFFVCWA | PYYVLQLTQL | SISRPTLTFV | YLYNAAISLG |
| dogMCH1R | TKRVTRTAIA | ICLVFFVCWA | PYYVLQLTQL | SISRPTLTFV | YLYNAAISLG |
| ratMCH1R | TKRVTRTAIA | ICLVFFVCWA | PYYVLQLTQL | SISRPTLTFV | YLYNAAISLG |

|          | 301        |            |            |            | 350        |
|----------|------------|------------|------------|------------|------------|
| huMCH1R  | YANSCLNPFV | YIVLCETFRK | RLVLSVKPAA | QGQLRAVSNA | QTADEERTES |
| dogMCH1R | YANSCLNPFV | YIVLCETFRK | RLVLSVKPAA | QGQLRAVSNA | QTADEERTES |
| ratMCH1R | YANSCLNPFV | YIVLCETFRK | RLVLSVKPAA | QGQLRTVSNA | QTADEERTES |

|          | 351 |
|----------|-----|
| huMCH1R  | KGT |
| dogMCH1R | KGT |
| ratMCH1R | KGT |

Fig. 1

```
              1                                                    50
huMCH1R       ATGGACCTGG AAGCCTCGCT GCTGCCCACT GGTCCCAACG CCAGCAACAC
dogMCH1R      ATGGACCTGG AAGCCTCGCT GCTGCCCCCC GGCCCCAACG CCAGCAACAC
ratMCH1R      ATGGATCTGC AAACCTCGTT GCTGTCCACT GGCCCCAATG CCAGCAACAT 51                                                   100
huMCH1R       CTCTGATGGC CCCGATAACC TCACTTCGGC AGGATCACCT CCTCGCACGG
dogMCH1R      CTCGGAGGGC CCGGACAACC TCACCTCTGC CGGGCCACCT CGTCGCACAG
ratMCH1R      CTCCGATGGC CAGGATAATC TCACATTGCC GGGGTCACCT CCTCGCACAG 101                                                  150
huMCH1R       GGAGCATCTC CTACATCAAC ATCATCATGC CTTCGGTGTT CGGCACCATC
dogMCH1R      GGAATGTCTC CTACATCAAC ATCATCATGC CTTCCGTGTT CGGCACCATC
ratMCH1R      GGAGTGTCTC CTACATCAAC ATCATTATGC CTTCCGTGTT TGGTACCATC 151                                                  200
huMCH1R       TGCCTCCTGG GCATCATCGG GAACTCCACG GTCATCTTCG CGGTCGTGAA
dogMCH1R      TGCCTGCTGG GTATCATCGG GAACTCCACA GTCATCTTCG CGGTGGTGAA
ratMCH1R      TGTCTCCTGG GCATCGTGGG AAACTCCACG GTCATCTTTG CTGTGGTGAA 201                                                  250
huMCH1R       GAAGTCCAAG CTGCACTGGT GCAACAACGT CCCCGACATC TTCATCATCA
dogMCH1R      GAAGTCCAAA CTGCACTGGT GCAGCAATGT CCCCGACATC TTTATCATCA
ratMCH1R      GAAGTCCAAG CTACACTGGT GCAGCAACGT CCCCGACATC TTCATCATCA 251                                                  300
huMCH1R       ACCTCTCGGT AGTAGATCTC CTCTTTCTCC TGGGCATGCC CTTCATGATC
dogMCH1R      ACCTCTCGGT GGTAGACCTC CTCTTTCTCC TGGGCATGCC CTTCATGATC
ratMCH1R      ACCTCTCTGT GGTGGATCTG CTCTTCCTGC TGGGCATGCC TTTCATGATC 301                                                  350
huMCH1R       CACCAGCTCA TGGGCAATGG GGTGTGGCAC TTTGGGGAGA CCATGTGCAC
dogMCH1R      CACCAGCTCA TGGGCAATGG TGTTTGGCAT TTTGGAGAGA CCATGTGCAC
ratMCH1R      CACCAGCTCA TGGGGAACGG CGTCTGGCAC TTTGGGGAAA CCATGTGCAC 351                                                  400
huMCH1R       CCTCATCACG GCCATGGATG CCAATAGTCA GTTCACCAGC ACCTACATCC
dogMCH1R      ACTCATCACG GCCATGGACG CCAACAGTCA ATTCACCAGC ACCTACATCC
ratMCH1R      CCTCATCACA GCCATGGACG CCAACAGTCA GTTCACTAGC ACCTACATCC 401                                                  450
huMCH1R       TGACCGCCAT GGCCATTGAC CGCTACCTGG CCACTGTCCA CCCCATCTCT
dogMCH1R      TGACCGCCAT GGCCATTGAC CGCTACCTGG CCACTGTCCA CCCCATCTCC
ratMCH1R      TGACTGCCAT GACCATTGAC CGCTACTTGG CCACCGTCCA CCCCATCTCC 451                                                  500
huMCH1R       TCCACGAAGT TCCGGAAGCC CTCTGTGGCC ACCCTGGTGA TCTGCCTCCT
dogMCH1R      TCCACCAAGT TCCGGAAGCC CTCTGTGGCC ACCCTGGTGA TCTGCCTCCT
ratMCH1R      TCCACCAAGT TCCGGAAGCC CTCCATGGCC ACCCTGGTGA TCTGCCTCCT
```

Fig. 2A

|          | 501 | | | | 550 |
|----------|-----|---|---|---|-----|
| huMCH1R  | GTGGGCCCTC | TCCTTCATCA | GCATCACCCC | TGTGTGGCTG | TATGCCAGAC |
| dogMCH1R | ATGGGCCCTC | TCATTCATCA | GCATCACCCC | CGTGTGGCTC | TACGCTAGGC |
| ratMCH1R | GTGGGCGCTC | TCCTTCATCA | GTATCACCCC | TGTGTGGCTC | TACGCCAGGC |

|          | 551 | | | | 600 |
|----------|-----|---|---|---|-----|
| huMCH1R  | TCATCCCCTT | CCCAGGAGGT | GCAGTGGGCT | GCGGCATACG | CCTGCCCAAC |
| dogMCH1R | TTATCCCCTT | CCCAGGGGGC | ACAGTGGGCT | GTGGCATCCG | CCTGCCCAAC |
| ratMCH1R | TCATTCCCTT | CCCAGGGGGT | GCTGTGGGCT | GTGGCATCCG | CCTGCCAAAC |

|          | 601 | | | | 650 |
|----------|-----|---|---|---|-----|
| huMCH1R  | CCAGACACTG | ACCTCTACTG | GTTCACCCTG | TACCAGTTTT | TCCTGGCCTT |
| dogMCH1R | CCAGACACTG | ACCTTTACTG | GTTCACCCTG | TACCAGTTCT | TCCTGGCCTT |
| ratMCH1R | CCGGACACTG | ACCTCTACTG | GTTCACTCTG | TACCAGTTTT | TCCTGGCCTT |

|          | 651 | | | | 700 |
|----------|-----|---|---|---|-----|
| huMCH1R  | TGCCCTGCCT | TTTGTGGTCA | TCACAGCCGC | ATACGTGAGG | ATCCTGCAGC |
| dogMCH1R | TGCCCTGCCC | TTCGTGGTCA | TCACAGCCGC | GTATGTGAGG | ATCCTGCAGC |
| ratMCH1R | TGCCCTTCCG | TTTGTGGTCA | TTACCGCCGC | ATACGTGAAA | ATACTACAGC |

|          | 701 | | | | 750 |
|----------|-----|---|---|---|-----|
| huMCH1R  | GCATGACGTC | CTCAGTGGCC | CCCGCCTCCC | AGCGCAGCAT | CCGGCTGCGG |
| dogMCH1R | GCATGATGTC | CTCGGTAGCC | CCTGCCTCTC | AACGCAGCAT | CCGGCTGCGG |
| ratMCH1R | GCATGACGTC | TTCGGTGGCC | CCAGCCTCCC | AACGCAGCAT | CCGGCTTCGG |

|          | 751 | | | | 800 |
|----------|-----|---|---|---|-----|
| huMCH1R  | ACAAAGAGGG | TGACCCGCAC | AGCCATCGCC | ATCTGTCTGG | TCTTCTTTGT |
| dogMCH1R | ACAAAGAGGG | TGACTCGCAC | GGCCATTGCC | ATCTGCCTGG | TCTTCTTCGT |
| ratMCH1R | ACAAAGAGGG | TGACCCGCAC | GGCCATTGCC | ATCTGTCTGG | TCTTCTTTGT |

|          | 801 | | | | 850 |
|----------|-----|---|---|---|-----|
| huMCH1R  | GTGCTGGGCA | CCCTACTATG | TGCTACAGCT | GACCCAGTTG | TCCATCAGCC |
| dogMCH1R | GTGCTGGGCT | CCCTACTATG | TGCTACAGTT | GACCCAGTTG | TCCATCAGCC |
| ratMCH1R | GTGCTGGGCA | CCCTACTATG | TGCTGCAGCT | GACCCAGCTG | TCCATCAGCC |

|          | 851 | | | | 900 |
|----------|-----|---|---|---|-----|
| huMCH1R  | GCCCGACCCT | CACCTTTGTC | TACTTATACA | ATGCGGCCAT | CAGCTTGGGC |
| dogMCH1R | GCCCGACACT | CACCTTTGTC | TACCTGTACA | ACGCAGCCAT | CAGCTTGGGC |
| ratMCH1R | GCCCGACCCT | CACGTTTGTC | TACTTGTACA | ACGCGGCCAT | CAGCTTGGGC |

|          | 901 | | | | 950 |
|----------|-----|---|---|---|-----|
| huMCH1R  | TATGCCAACA | GCTGCCTCAA | CCCCTTTGTG | TACATCGTGC | TCTGTGAGAC |
| dogMCH1R | TATGCCAACA | GCTGCCTAAA | CCCCTTTGTG | TACATCGTGC | TCTGTGAGAC |
| ratMCH1R | TATGCTAACA | GCTGCCTGAA | CCCCTTTGTG | TACATAGTGC | TCTGTGAGAC |

|          | 951 | | | | 1000 |
|----------|-----|---|---|---|------|
| huMCH1R  | GTTCCGCAAA | CGCTTGGTCC | TGTCGGTGAA | GCCTGCAGCC | CAGGGGCAGC |
| dogMCH1R | ATTCCGCAAG | CGCTTGGTCC | TGTCGGTGAA | GCCTGCCGCC | CAGGGGCAGC |
| ratMCH1R | CTTTCGAAAA | CGCTTGGTGT | TGTCAGTGAA | GCCTGCAGCC | CAGGGGCAGC |

Fig. 2B

```
         1001                                                  1050
huMCH1R  TTCGCGCTGT CAGCAACGCT CAGACGGCTG ACGAGGAGAG GACAGAAAGC
dogMCH1R TTCGAGCCGT CAGCAATGCT CAGACAGCTG ATGAGGAGAG GACAGAAAGC
ratMCH1R TCCGCACGGT CAGCAACGCT CAGACAGCTG ATGAGGAGAG GACAGAAAGC 1051       1062
huMCH1R  AAAGGCACCT GA
dogMCH1R AAAGGCACCT GA
ratMCH1R AAAGGCACCT GA
```

Fig. 2C

DOG MELANIN-CONCENTRATING HORMONE RECEPTOR

CROSS-REFERENCE TO RELATED APPLICATIONS

The present application claims priority to provisional application U.S. Ser. No. 60/219,669, filed Jul. 21, 2000, hereby incorporated by reference herein.

BACKGROUND OF THE INVENTION

The references cited herein are not admitted to be prior art to the claimed invention.

Neuropeptides present in the hypothalamus play a major role in mediating the control of body weight. (Flier et al., 1998, *Cell*, 92, 437–440.) Melanin-concentrating hormone (MCH) is a cyclic 19-amino acid neuropeptide synthesized as part of a larger pre-prohormone precursor in the hypothalamus that also encodes neuropeptides NEI and NGE. (Nahon et al., 1990, *Mol. Endocrinol.*, 4, 632–637.) MCH was first identified in salmon pituitary, and in fish MCH affects melanin aggregation thus affecting skin pigmentation. In trout and in eels MCH has also been shown to be involved in stress induced or CRF-stimulated ACTH release. (Kawauchi et al., 1983, *Nature*, 305, 321–323.)

In humans two genes encoding MCH have been identified that are expressed in the brain. (Breton et al., 1993, *Mol. Brain Res.*, 18, 297–310.) In mammals MCH has been localized primarily to neuronal cell bodies of the hypothalamus which are implicated in the control of food intake, including perikarya of the lateral hypothalamus and zona inertia. (Knigge et al., 1996, *Peptides*, 17, 1063–1073.)

Pharmacological and genetic evidence suggest that the primary mode of MCH action is to promote feeding (orexigenic). MCH mRNA is up regulated in fasted mice and rats and in the ob/ob mouse. (Qu et al., 1996, *Nature*, 380, 243–247.) Injection of MCH centrally (ICV) stimulates food intake and MCH antagonizes the hypophagic effects seen with α-melanocyte stimulating hormone (αMSH). (Qu et al., 1996, *Nature*, 380, 243–247.) MCH-deficient mice are lean, hypophagic, and have increased metabolic rate. (Shimada et al., 1998, *Nature*, 396, 670–673.)

MCH action is not limited to modulation of food intake as effects on the hypothalamic-pituitary-axis have been reported. (Nahon, 1994, *Critical Rev. in Neurobiol.*, 8, 221–262.) MCH may be involved in the body response to stress as MCH can modulate the stress-induced release of CRF from the hypothalamus and ACTH from the pituitary. In addition, MCH neuronal systems may be involved in reproductive or maternal function.

Several references describe a receptor that is indicated to bind MCH. (Chambers et al., 1999, *Nature*, 400, 261–265; Saito et al., 1999, *Nature*, 400, 265–269; Bächner et al., 1999, *FEBS Letters*, 457, 522–524; Shimomura et al., 1999, *Biochemical and Biophysical Research Communications*, 261, 622–626; and Lembo et al., 1999, *Nat. Cell Biol.*, 1, 267–271.)

SUMMARY OF THE INVENTION

The present invention features polypeptides and nucleic acids related to a dog MCH receptor and uses of such polypeptides and nucleic acids. The dog MCH receptor is a G protein coupled receptor whose activity is stimulated by MCH binding.

Polypeptides related to a dog MCH receptor contain a region of at least 9 contiguous amino acids that is present in a dog MCH receptor. Such polypeptides may contain additional regions including regions present, or not present, in a dog MCH receptor.

Nucleic acids related to a dog MCH receptor contain a region of at least 18 contiguous nucleotides that is present in a dog MCH receptor nucleic acid. Such nucleic acids may contain additional regions including regions present, or not present, in a dog MCH receptor nucleic acid.

Thus, a first aspect of the present invention describes a purified polypeptide comprising a unique amino acid region of a dog MCH receptor. The unique region is at least 9 amino acids in length.

A "unique amino acid region" of a dog MCH receptor is a region of contiguous amino acids present in SEQ. ID. NO. 1 that is not present in SEQ. ID. NOs. 2 or 3. SEQ. ID. NO. 1, which is referred to herein as a dog MCH receptor, was derived from dog nucleic acid using a human primer and may thus contain one or more N-terminal amino acids corresponding to a human source rather than a dog source. SEQ. ID. NO. 2 is a human MCH receptor amino acid sequence and SEQ. ID. NO. 3 is a rat MCH receptor amino acid sequence. The unique region may contain segments of contiguous amino acids present in SEQ. ID. NOs. 2 or 3 smaller than the indicated unique region size.

A "purified polypeptide" represents at least 10% of the total protein present in a sample or preparation. In preferred embodiments, the purified polypeptide represents at least about 50%, at least about 75%, or at least about 95% of the total protein in a sample or preparation. Reference to "purified polypeptide" does not require that the polypeptide has undergone any purification and may include, for example, chemically synthesized polypeptide that has not been purified.

Another aspect of the present invention describes a purified nucleic acid comprising a nucleotide sequence encoding for a unique amino acid region from a dog MCH receptor. The encoded for region is at least 9 amino acids in length.

A "purified nucleic acid" represents at least 10% of the total nucleic acid present in a sample or preparation. In preferred embodiments, the purified nucleic acid represents at least about 50%, at least about 75%, or at least about 95% of the total nucleic acid in a sample or preparation. Reference to "purified nucleic acid" does not require that the nucleic acid has undergone any purification and may include, for example, chemically synthesized nucleic acid that has not been purified.

Another aspect of the present invention describes a purified nucleic acid comprising a unique nucleotide sequence region of a dog MCH receptor nucleic acid sequence, or the complement thereof. The unique nucleotide sequence region is at least 18 nucleotides in length.

A "unique nucleotide sequence region" of a dog MCH receptor nucleic acid is a region that comprises at least 18 contiguous nucleotides of SEQ. ID. NO. 4 that is not present in SEQ. ID. NOs. 5 or 6. SEQ. ID. NO. 4, which is referred to herein as a nucleotide sequence encoding for a dog MCH receptor, was derived from dog nucleic acid using a human primer and may thus contain one or more 5' nucleotides corresponding to a human source rather than a dog source. SEQ. ID. NO. 5 is the nucleotide sequence encoding for a human MCH receptor and SEQ. ID. NO. 6 is the nucleotide sequence encoding for a rat MCH receptor. The unique region may contain segments of contiguous nucleotides present in SEQ. ID. NOs. 5 or 6 smaller than the indicated unique region size.

Another aspect of the present invention describes a nucleic acid comprising a recombinant nucleotide sequence encoding for a unique amino acid region of a dog MCH receptor. In different embodiments the nucleic acid is an expression vector or is part of a host genome.

A "recombinant nucleotide sequence" is a sequence that is present on a nucleic acid containing one or more nucleic acid regions not naturally associated with that sequence. Examples of such regions that may be present with the sequence include one or more regulatory elements not naturally associated with the sequence, viral elements, and selectable markers.

Another aspect of the present invention describes a recombinant cell comprising an expression vector encoding for a unique amino acid region of a dog MCH receptor. The expression vector contains a promoter that is functionally coupled to nucleic acid encoding for the unique region and is recognized by an RNA polymerase present in the cell.

Another aspect of the present invention describes a recombinant cell made by introducing an expression vector encoding for a unique amino acid region of a dog MCH receptor into a cell. The expression vector can be used to insert the dog nucleic acid into the genome of the host, or can exist as an autonomous piece of nucleic acid.

Another aspect of the present invention describes a method of measuring the ability of a test compound to affect MCH receptor activity. The method involves providing the compound to a recombinant cell expressing a functional MCH receptor containing a unique dog amino acid region from a recombinant nucleic acid and measuring MCH receptor activity. Preferably, the recombinant nucleic acid is present on an expression vector.

Another aspect of the present invention describes a method of producing a MCH receptor polypeptide. The method involves the step of growing a recombinant cell able to express a dog MCH receptor polypeptide under conditions wherein the polypeptide is expressed from an expression vector.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

BRIEF DESCRIPTION OF THE DRAWINGS

FIG. 1 illustrates a comparison of the amino acid sequence for a dog MCH receptor (SEQ. ID. NO. 1), a human MCH receptor (SEQ. ID. NO. 2), and a rat MCH receptor (SEQ. ID. NO. 3).

FIGS. 2A–2C illustrate a comparison of the nucleotide sequence encoding for a dog MCH receptor (SEQ. ID. NO. 4), a human MCH receptor (SEQ. ID. NO. 5), and a rat MCH receptor (SEQ. ID. NO. 6).

DETAILED DESCRIPTION OF THE INVENTION

Polypeptides and nucleic acids related to a dog MCH receptor are preferably used in an in vitro functional assay measuring whether a compound acts differently at the dog receptor than at the human receptor, or affects MCH receptor activity. Such assays can be used to help evaluate whether a dog model provides a useful test system in looking for a human therapeutic compound and for assaying for compounds active at the MCH receptor.

The MCH receptor provides a target to achieve different beneficial effects in a patient. Preferably, MCH receptor activity is modulated to achieve one or more of the following: weight loss, weight gain, treat cancer (e.g., colon or breast), reduce pain, treat diabetes, reduce stress, or teat sexual dysfunction.

Modulation of MCH receptor activity can be achieved by evoking a response at the MCH receptor or by altering a response evoked by an MCH receptor agonist or antagonist. Compounds modulating MCH receptor activity include agonists, antagonists, and allosteric modulators. Generally, MCH receptor antagonists and allosteric modulators negatively affecting activity will be used to achieve weight loss, treat cancer (e.g., colon or breast), reduce pain, reduce stress, and/or teat sexual dysfunction; and MCH receptor agonists and allosteric modulators positively affecting activity will be used to produce a weight gain.

Preferably, MCH receptor activity is modulated to achieve a weight loss or to treat diabetes in a patient. Diabetes mellitus can be treated by modulating MCH receptor activity to achieve, for example, one or both of the following: enhancing glucose tolerance or decreasing insulin resistance.

Excessive body weight is a contributing factor to different diseases, including hypertension, diabetes, dyslipidemias, cardiovascular disease, gall stones, osteoarthritis, and certain forms of cancers. Bringing about a weight loss can be used, for example, to reduce the likelihood of such diseases and as part of a treatment for such diseases. Weight reduction can be achieved by modulating MCH receptor activity to obtain, for example, one or more of the following effects: reducing appetite, increasing metabolic rate, reducing fat intake, or reducing carbohydrate craving.

Facilitating a weight gain, maintenance in weight, or appetite increase is particularly useful for a patient having a disease or disorder, or under going a treatment, accompanied by weight loss. Examples of diseases or disorders accompanied by weight loss include anorexia, bulimia, cancer cachexia, AIDS, wasting, cachexia, and wasting in frail elderly. Examples of treatments accompanied by weight loss include chemotherapy, radiation therapy, temporary or permanent immobilization, and dialysis.

MCH Receptor Related Polypeptides

Polypeptides related to the dog MCH receptor preferably contain a unique dog amino acid region. In addition to the unique amino acid region, regions that may, or may not, be related to the dog MCH receptor polypeptide may be present. Such polypeptides have a variety of uses, such as providing a component of a functional MCH receptor; being used as an immunogen to produce antibodies binding to the MCH receptor; being used as a target to identify compounds binding to the MCH receptor; and/or being used in assays measuring the ability of a compound to affect MCH receptor activity.

Unique dog amino acid regions can readily be identified based on a comparison of the dog MCH receptor sequence described herein, with the human and rat MCH receptor amino acid sequences. Such a sequence comparison is illustrated in FIG. 1. Examples of unique dog amino acid regions include the following:

| | |
|---|---|
| LEASLLPPGP, | SEQ. ID. NO. 7 |
| SEGPDNLTSAGP, | SEQ. ID. NO. 8 |
| RRTGNVSYIN, | SEQ. ID. NO. 9 |
| PFPGGTVGCG, and | SEQ. ID. NO. 10 |
| ILQRMMSSVA. | SEQ. ID. NO. 11 |

The definition of unique amino acid region is with respect to the human and rat MCH receptors. Thus, a unique amino acid region may be present in a MCH receptor amino acid sequence from one or more species other than the human or rat sequences, or in a non-MCH receptor sequence.

In different embodiments a dog MCH receptor related polypeptide comprises or consists of a unique amino acid region at least 18, at least 27, or at least 54, amino acids in length. Preferably, the dog MCH receptor related polypeptide comprises or consists of the amino acid sequence of SEQ. ID. NO. 1.

Polypeptides can be produced using standard techniques including those involving chemical synthesis and those involving biochemical synthesis. Techniques for chemical synthesis of polypeptides are well known in the art. (See e.g., Vincent, in *Peptide and Protein Drug Delivery*, New York, N.Y., Dekker, 1990.)

Biochemical synthesis techniques for polypeptides are also well known in the art. Such techniques employ a nucleic acid template for polypeptide synthesis. The genetic code providing the sequences of nucleic acid triplets coding for particular amino acids is well known in the art. (See, e.g., Lewin *GENES IV*, p. 119, Oxford University Press, 1990.) Examples of techniques for introducing nucleic acid into a cell and expressing the nucleic acid to produce protein are provided in references such as Ausubel, *Current Protocols in Molecular Biology*, John Wiley, 1987–1998, and Sambrook et al., in *Molecular Cloning, A Laboratory Manual*, 2$^{nd}$ Edition, Cold Spring Harbor Laboratory Press, 1989.

Functional MCH Receptor Derivatives

Functional MCH receptors are stimulated by MCH binding. Functional MCH receptors include the MCH receptor of SEQ. ID. NO. 1, and receptors having MCH receptor activity and containing a unique dog amino acid region as a component.

Starting with a MCH receptor obtained from a particular source, derivatives can be produced having MCH receptor activity. Such derivatives include polypeptides with amino acid substitutions, additions and deletions. Changes made to produce functional derivatives should be made outside of the MCH binding domain and in a manner not altering the tertiary structure. The ability of a polypeptide to have MCH receptor activity can be confirmed using techniques such as those measuring G-protein activity.

The sequence comparison provided in FIG. 1 illustrates amino acids that vary between the human, rat, and dog MCH receptor. Such variable amino acids are good targets for alterations.

Additionally, amino acids are classified into certain types based on the structure of their R-groups. Substituting different amino acids within a particular group, such as substituting valine for leucine, arginine for lysine, and asparagine for glutamine may not cause a change in functionality of the polypeptide.

MCH Antibodies

Antibodies recognizing a dog MCH receptor polypeptide can be produced using a polypeptide of SEQ. ID. NO. 1 or a fragment thereof as an immunogen. Fragments should be at least 9 amino acids in length and preferably contain a unique amino acid region.

Antibodies to the MCH receptor have different uses such as being used to identify the presence of MCH receptor polypeptides and for isolating MCH receptor polypeptides. Examples of techniques for producing and using antibodies are described in Ausubel *Current Protocols in Molecular Biology*, John Wiley, 1987–1998, Harlow et al., *Antibodies, A Laboratory Manual*, Cold Spring Harbor Laboratory, 1988, and Kohler et al., 1975, *Nature*, 256, 495–497.

Binding Assays

Assays measuring the ability of a compound to bind the dog MCH receptor can be performed using a polypeptide of SEQ. ID. NO. 1 or a fragment thereof as a target. Fragments should be at least 9 amino acids in length and contain a site to which either an agonist, antagonist, or allosteric modulator binds. Different types of assay formats can be employed including competitive and non-competitive assays.

Compounds identified as binding to a full-length receptor or a receptor fragment can be used to determine the locus of a binding site by testing the ability of the compound to bind to smaller length fragments. For example, MCH binds to the MCH receptor and labeled MCH can be used to identify that portion of the receptor to which MCH binds. Fragments identified as containing a compound binding site can be used to test for additional compounds that bind to the binding site.

Preferred polypeptide fragments used in a binding assay consist of a unique amino acid region. However, fragments containing additional amino acid sequences can be employed, for example, to facilitate attachment to a column.

Binding assays can be performed using individual compounds or preparations containing different compounds. A preparation containing different compounds wherein one or more compounds bind to the MCH receptor can be divided into smaller groups to identify compound(s) binding to the MCH receptor. In an embodiment of the present invention a test preparation containing at least 10 compounds is used in a binding assay.

Binding assays can be performed using recombinantly produced MCH receptor polypeptides present in different environments. Such environments include, for example, cell extracts and purified cell extracts containing the MCH receptor polypeptide expressed from recombinant nucleic acid; and the use of a purified MCH receptor polypeptide produced by recombinant means which is introduced into a different environment.

Functional Assays

Assays involving functional dog MCH receptors and chimeric receptors can be employed to select for compounds active at the MCH receptor and to evaluate the ability of a compound to affect receptor activity. MCH receptor activity can be measured using different techniques such as detecting a change in the intracellular conformation of the MCH receptor, measuring G protein activity, or measuring the level of intracellular messengers.

Recombinantly expressed MCH receptor polypeptides can be used to facilitate determining whether a compound is active at the MCH receptor or another receptor. For example, the MCH receptor can be expressed by an expression vector in a cell line such as HEK 293, COS 7, and CHO not normally expressing the receptor, wherein the same cell line without the expression vector or with an expression vector not encoding a MCH receptor can act as a control.

MCH receptor activity can be measured, for example, by assays measuring the phospholipase C signal transduction pathway. Activity of the phospholipase C signal transduction pathway can be measured using standard techniques such as those measuring intracellular $Ca^{2+}$. Examples of techniques well known in the art that can be employed to measure $Ca^{2+}$ include the use of dyes such as Fura-2 and the use of $Ca^{2+}$-bioluminescent sensitive reporter proteins such as aequorin. An example of a cell line employing aequorin to measure G protein activity is HEK293/aeq17. (Button et al., 1993, *Cell Calcium*, 14, 663–671, and Feighner et al., 1999, *Science*, 284, 2184–2188, both of which are hereby incorporated by reference herein.)

Chimeric receptors containing one or more MCH receptor regions functionally coupled to polypeptides from other G proteins can also be used to measure activity. A chimeric MCH receptor contains an N-terminal extracellular domain; a transmembrane domain made up of transmembrane regions, extracellular loop regions, and intracellular loop regions; and an intracellular carboxy terminus domain. Preferred chimerics contain one or more of these different domains from a dog MCH receptor.

The specificity of G protein coupling is determined by intracellular domain(s). A chimeric G protein coupled receptor can be produced to functionally couple to a particular G protein. For example a G protein that normally couples to Gs can be coupled to Gq or Gi allowing for the detection of receptor activity by measuring Gq or Gi activity. Techniques for producing chimeric receptors and measuring G protein coupled responses are provided for in, for example, International Application No. WO 97/05252, and U.S. Pat. No. 5,264,565, both of which are hereby incorporated by reference herein.

Functional assays can be performed using individual compounds or preparations containing different compounds. A preparation containing different compounds where one or more compounds affect MCH receptor or chimeric receptor activity can be divided into smaller groups of compounds to identify the compound(s) affecting MCH receptor activity. In an embodiment of the present invention a test preparation containing at least 10 compounds is used in a functional assay.

Functional assays can be performed using recombinantly produced MCH receptor polypeptides or chimeric receptor polypeptides present in different environments. Such environments include, for example, cell extracts, and purified cell extracts, containing the MCH receptor polypeptide expressed from recombinant nucleic acid; and the use of a purified MCH receptor polypeptide produced by recombinant means that is introduced into a different environment.

MCH Receptor Related Nucleic Acid

Nucleic acids related to the dog MCH receptor nucleic acid preferably contain a unique dog nucleotide sequence region or the complement thereof. Such nucleic acids have a variety of uses, such as being used as a hybridization probe or PCR primer to identify the presence of dog MCH nucleic acid; being used as a hybridization probe or PCR primer to identify or clone nucleic acid encoding for receptors related to the MCH receptor from different sources; and/or being used for recombinant expression of a dog MCH receptor polypeptide.

Unique dog nucleic acid regions can readily be identified based on a comparison of the dog MCH receptor nucleic acid sequences described herein, with the human and the rat MCH receptor nucleic acid sequences. Such a sequence comparison is illustrated in FIGS. 2A–2C.

Examples of unique dog nucleic acid regions include the following:

```
SEQ. ID. NO. 12    CCTCGGAGGGCCCGGACAACC,
SEQ. ID. NO. 13    ACCTCTGCCGGGCCACCTCGT,
SEQ. ID. NO. 14    GCCCTTCGTGGTCATCACAGCCGCGTAT,
SEQ. ID. NO. 15    TGTCCTCGGTAGCCCCTGCCTCTCAA, and
SEQ. ID. NO. 16    TTCGAGCCGTCAGCAATGCT.
```

The guidance provided in the present application can be used to obtain the nucleic acid sequence encoding the full-length dog MCH receptor, to obtain nucleic acids encoding for MCH receptors from additional sources, and to artificially produce a MCH receptor. Obtaining nucleic acids encoding a MCH receptor from different sources is facilitated using sets of degenerative probes and primers and by the proper selection of hybridization conditions. Sets of degenerative probes and primers are produced taking into account the degeneracy of the genetic code. Adjusting hybridization conditions is useful for controlling probe or primer specificity to allow for hybridization to nucleic acids having similar sequences.

Techniques employed for hybridization detection and PCR cloning are well known in the art. Nucleic acid detection techniques are described, for example, in Sambrook et al., in *Molecular Cloning, A Laboratory Manual*, $2^{nd}$ Edition, Cold Spring Harbor Laboratory Press, 1989. PCR cloning techniques are described, for example, in White, *Methods in Molecular Cloning*, volume 67, Humana Press, 1997.

MCH receptor probes and primers can be used to screen nucleic acid libraries containing, for example, genomic DNA or cDNA. Such libraries are commercially available, and can be produced using techniques such as those described in Ausubel, *Current Protocols in Molecular Biology*, John Wiley, 1987–1998.

Starting with a particular amino acid sequence and the known degeneracy of the genetic code, a large number of different encoding nucleic acid sequences can be obtained. The degeneracy of the genetic code arises because almost all amino acids are encoded by different combinations of nucleotide triplets or "codons". The translation of a particular codon into a particular amino acid is well known in the art (see, e.g., Lewin *GENES IV*, p. 119, Oxford University Press, 1990). Amino acids are encoded by codons as follows:

A=Ala=Alanine: codons GCA, GCC, GCG, GCU
C=Cys=Cysteine: codons UGC, UGU
D=Asp=Aspartic acid: codons GAC, GAU
E=Glu=Glutamic acid: codons GAA, GAG
F=Phe=Phenylalanine: codons WJC, UUU
G=Gly=Glycine: codons GGA, GGC, GGG, GGU
H=His=listidine: codons CAC, CAU
I=Ile=Isoleucine: codons AUA, AUC, AUU
K=Lys=Lysine: codons AAA, AAG
L=Leu=Leucine: codons UUA, UUG, CUA, CUC, CUG, CUU
M=Met=Methionine: codon AUG
N=Asn=Asparagine: codons AAC, AAU
P=Pro=Proline: codons CCA, CCC, CCG, CCU
Q=Gln=Glutamine: codons CAA, CAG R=Arg=Arginine: codons AGA, AGG, CGA, CGC, CGG, CGU S=Ser=Serine: codons AGC, AGU, UCA, UCC, UCG, UCU T=Thr=Threonine: codons ACA, ACC, ACG, ACU V=Val=Valine: codons GUA, GUC, GUG, GUU W=Trp=Tryptophan: codon UGG Y=Tyr=Tyrosine: codons UAC, UAU.

Nucleic acid having a desired sequence can be synthesized using chemical and biochemical techniques. Examples of chemical techniques are described in Ausubel, *Current Protocols in Molecular Biology*, John Wiley, 1987–1998, and Sambrook et al., in *Molecular Cloning, A Laboratory Manual*, $2^{nd}$ Edition, Cold Spring Harbor Laboratory Press, 1989.

Biochemical synthesis techniques involve the use of a nucleic acid template and appropriate enzymes such as DNA and/or RNA polymerases. Examples of such techniques include in vitro amplification techniques such as PCR and transcription based amplification, and in vivo nucleic acid replication. Examples of suitable techniques are provided by Ausubel, *Current Protocols in Molecular Biology*, John Wiley, 1987–1998, Sambrook et al., in *Molecular Cloning, A Laboratory Manual*, $2^{nd}$ Edition, Cold Spring Harbor Laboratory Press, 1989, and Kacian et al., U.S. Pat. No. 5,480,784.

In different embodiments dog MCH receptor related nucleic acid comprises or consists of a unique nucleic acid region, or the complement thereof, at least 27 or at least 54 bases in length. Preferably, the dog MCH receptor related nucleic acid comprises or consists of the nucleic acid sequence of SEQ. ID. NO. 4.

MCH Receptor Probes

Detection probes for the dog MCH receptor preferably contain a unique dog nucleic acid region, or the complement thereof. Such probes can contain additional nucleic acid that may, or may not, be complementary to dog MCH receptor nucleic acid. Preferably, additional nucleic acid that is present has a particular purpose such as providing for increased specificity, being a reporter sequence, or being a capture sequence. However, additional nucleic acid need not have a particular purpose.

Probes for the MCH receptor can specifically hybridize to MCH receptor target nucleic acid under appropriate hybridization conditions (i.e., distinguish target nucleic acid from one or more non-target nucleic acid molecules). A preferred non-target nucleic acid is either nucleic acid encoding for the human MCH receptor or the complement thereof. Hybridization occurs through complementary nucleotide bases present on the probe and MCH receptor nucleic acid. Hybridization conditions determine whether two molecules have sufficiently strong interactions with each other to form a stable hybrid.

Probes are composed of nucleic acids or derivatives thereof such as modified nucleic acid and peptide nucleic acid. Modified nucleic acid includes nucleic acid with one or more altered sugar groups, altered internucleotide linkages, and/or altered nucleotide purine or pyrimidine bases. References describing modified nucleic acid include International Publication No. WO 98/02582, U.S. Pat. No. 5,859,221 and U.S. Pat. No. 5,852,188, each of which are hereby incorporated by reference herein.

The degree of interaction between two molecules that hybridize together is reflected by the Tm of the produced hybrid. The higher the Tm the stronger the interactions and the more stable the hybrid. Tm is effected by numerous factors well known in the art such as the degree of complementarity, the type of complementary bases present (e.g., A-T hybridization versus G-C hybridization), the structure of the nucleic acid backbones, and solution components. E.g., Sambrook et al., in *Molecular Cloning, A Laboratory Manual*, $2^{nd}$ Edition, Cold Spring Harbor Laboratory Press, 1989.

Stable hybrids are formed when the Tm of a hybrid is greater than the temperature employed under a particular set of hybridization assay conditions. The degree of specificity of a probe can be varied by adjusting the hybridization stringency conditions. Detecting probe hybridization is facilitated through the use of a detectable label. Examples of detectable labels include luminescent, enzymatic, and radioactive labels.

Examples of stringency conditions are provided in Sambrook et al., in *Molecular Cloning, A Laboratory Manual*, $2^{nd}$ Edition, Cold Spring Harbor Laboratory Press, 1989. An example of high stringency conditions is as follows: Prehybridization of filters containing DNA is carried out for 2 hours to overnight at 65° C. in buffer composed of 6×SSC, 5× Denhardt's solution, and 100 µg/ml denatured salmon sperm DNA. Filters are hybridized for 12 to 48 hours at 65° C. in prehybridization mixture containing 100 µg/ml denatured salmon sperm DNA and 5–20×$10^6$ cpm of $^{32}$P-labeled probe. Washing of filters is done at 37° C. for 1 hour in a solution containing 2×SSC, 0.1% SDS. This is followed by a wash in 0.1×SSC, 0.1% SDS at 50° C. for 45 minutes before autoradiography. Other procedures using conditions of high stringency would include, for example, either a hybridization step carried out in 5×SSC, 5× Denhardt's solution, 50% formamide at 42° C. for 12 to 48 hours or a washing step carried out in 0.2×SSPE, 0.2% SDS at 65° C. for 30 to 60 minutes.

Recombinant Expression

MCH receptor related polypeptides can be expressed from recombinant nucleic acid in a suitable host or in a test tube using a translation system. Recombinantly expressed MCH receptor polypeptides are preferably used in assays to screen for compounds that bind to the MCH receptor and modulate the activity of the receptor.

Preferably, expression is achieved in a host cell using an expression vector. An expression vector contains recombinant nucleic acid encoding for a desired polypeptide along with regulatory elements for proper transcription and processing. The regulatory elements that may be present include those naturally associated with the recombinant nucleic acid and exogenous regulatory elements not naturally associated with the recombinant nucleic acid. Exogenous regulatory elements such as an exogenous promoter can be useful for expressing recombinant nucleic acid in a particular host.

Generally, the regulatory elements that are present include a transcriptional promoter, a ribosome binding site, a terminator, and an optionally present operator. Another preferred element is a polyadenylation signal providing for processing in eukaryotic cells. Preferably, an expression vector also contains an origin of replication for autonomous replication in a host cell, a selectable marker, a limited number of useful restriction enzyme sites, and a potential for high copy number. Examples of expression vectors are cloning vectors, modified cloning vectors, specifically designed plasmids and viruses.

Expression vectors that can be used to provide suitable levels of polypeptide expression in different hosts are well known in the art. Mammalian expression vectors well known in the art include pcDNA3 (Invitrogen), pMC1neo (Stratagene), pXT1 (Stratagene), pSG5 (Stratagene), EBO-pSV2-neo (ATCC 37593), pBPV-1(8-2) (ATCC 37110), pdBPV-MMTneo (342-12) (ATCC 37224), pRSVgpt (ATCC 37199), pRSVneo (ATCC 37198), pSV2-dhfr (ATCC 37146), pUCTag (ATCC 37460), pCI-neo (Promega) and .lambda.ZD35 (ATCC 37565). Bacterial expression vectors well known in the art include pET11a (Novagen), lambda gt11 (Invitrogen), pcDNAII (Invitrogen), and pKK223-3 (Pharmacia). Fungal cell expression vectors well known in the art include pYES2 (Invitrogen), Pichia expression vector (Invitrogen). Insect cell expression vectors well known in the art include Blue Bac III (Invitrogen).

Recombinant host cells may be prokaryotic or eukaryotic. Examples of recombinant host cells include the following: bacteria such as *E. coli*; fungal cells such as yeast; mammalian cells such as human, bovine, porcine, monkey and rodent; and insect cells such as *Drosophila* and silkworm derived cell lines. Commercially available mammalian cell lines include L cells L-M (TK.sup.-) (ATCC CCL 1.3), L cells L-M (ATCC CCL 1.2), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NTH/3T3 (ATCC CRL 1658), HeLa (ATCC CCL 2), C1271 (ATCC CRL 1616), BS-C-1 (ATCC CCL 26) and MRC-5 (ATCC. CCL 171).

Expression vectors may be introduced into host cells using standard techniques. Examples of such techniques include transformation, transfection, lipofection, protoplast fusion, and electroporation.

MCH receptor nucleic acid can be expressed in a cell without the use of an expression vector employing, for example, synthetic mRNA or native mRNA. Additionally, mRNA can be translated in various cell-free systems such as wheat germ extracts and reticulocyte extracts, as well as in cell based systems, such as frog oocytes. Introduction of mRNA into cell based systems can be achieved, for example, by microinjection.

EXAMPLES

Examples are provided below to further illustrate different features of the present invention. The examples also illustrate useful methodology for practicing the invention. These examples do not limit the claimed invention.

Example 1

Cloning of a Dog MCH Receptor

A complete coding sequence for a dog MCH receptor was obtained by RT-PCR and hybridization screening of a cDNA library (constructed in the mammalian expression vector pcDNA 3.1 (+); Invitrogen) prepared from dog hypothalamus poly (A)+mRNA. A forward (sense) PCR primer of SEQ. ID. NO. 17 (ATG GAC CTG) derived from a human MCH receptor sequence was used to amplify the dog MCH receptor. Thus, the resulting dog MCH receptor contains 6 amino acids (SEQ. ID. NO. 18: DLEASL) adjacent to the N-terminal methionine that may be similar or identical to those amino acids that correspond to the naturally occurring dog MCH receptor. The N terminal methionine (ATG) would be identical in both dog and human MCH receptors. The remaining 353 amino acids (amino acid 8 to 353) were from a dog MCH receptor.

The dog MCH receptor protein sequence is highly related to the human and rat MCH receptor of SEQ. ID. NOs. 2 and 3. The percent protein sequence identity to the human and rat MCH receptors is 97.5% and 94.6%, respectively.

The amino acid and encoding nucleotide sequences for the dog MCH receptor is as follows:

```
Dog MCH Receptor Amino Acid Sequence:

MDLEASLLPPGPNASNTSEGPDNLTSAGPPRRTGNVSYINIIMPSVFGTICLLGII      SEQ. ID. NO. 1

GNSTVIFAVVKKSKLHWCSNVPDIFIINLSVVDLLFLLGMPFMIHQLMGNGVW

HFGETMCTLITAMDANSQFTSTYILTAMAIDRYLATVHPISSTKFRKPSVATLV

ICLLWALSFISITPVWLYARLIPFPGGTVGCGIRLPNPDTDLYWFTLYQFFLAFA

LPFVVITAAYVRILQRMMSSVAPASQRSIRLRTKRVTRTAIAICLVFFVCWAPY

YVLQLTQLSISRPTLTFVYLYNAAISLGYANSCLNPFVYIVLCETFRKRLVLSV

KPAAQGQLRAVSNAQTADEERTESKGT

Dog MCH Receptor Encoding Nucleotide Sequence (including stop codon):

ATGGACCTGGAAGCCTCGCTGCTGCCCCCCGGCCCCAACGCCAGCAACAC            SEQ. ID. NO. 4

CTCGGAGGGCCCGGACAACCTCACCTCTGCCGGGCCACCTCGTCGCACAG

GGAATGTCTCCTACATCAACATCATCATGCCTTCCGTGTTCGGCACCATCT

GCCTGCTGGGTATCATCGGGAACTCCACAGTCATCTTCGCGGTGGTGAAG

AAGTCCAAACTGCACTGGTGCAGCAATGTCCCCGACATCTTTATCATCAA

CCTCTCGGTGGTAGACCTCCTCTTTCTCCTGGGCATGCCCTTCATGATCCA

CCAGCTCATGGGCAATGGTGTTTGGCATTTTGGAGAGACCATGTGCACAC

TCATCACGGCCATGGACGCCAACAGTCAATTCACCAGCACCTACATCCTG

ACCGCCATGGCCATTGACCGCTACCTGGCCACTGTCCACCCCATCTCCTCC
```

-continued

```
ACCAAGTTCCGGAAGCCCTCTGTGGCCACCCTGGTGATCTGCCTCCTATGG

GCCCTCTCATTCATCAGCATCACCCCCGTGTGGCTCTACGCTAGGCTTATC

CCCTTCCCAGGGGGCACAGTGGGCTGTGGCATCCGCCTGCCCAACCCAGA

CACTGACCTTTACTGGTTCACCCTGTACCAGTTCTTCCTGGCCTTTGCCCTG

CCCTTCGTGGTCATCACAGCCGCGTATGTGAGGATCCTGCAGCGCATGAT

GTCCTCGGTAGCCCCTGCCTCTCAACGCAGCATCCGGCTGCGGACAAAGA

GGGTGACTCGCACGGCCATTGCCATCTGCCTGGTCTTCTTCGTGTGCTGGG

CTCCCTACTATGTGCTACAGTTGACCCAGTTGTCCATCAGCCGCCCGACAC

TCACCTTTGTCTACCTGTACAACGCAGCCATCAGCTTGGGCTATGCCAACA

GCTGCCTAAACCCCTTTGTGTACATCGTGCTCTGTGAGACATTCCGCAAGC

GCTTGGTCCTGTCGGTGAAGCCTGCCGCCCAGGGGCAGCTTCGAGCCGTC

AGCAATGCTCAGACAGCTGATGAGGAGAGGACAGAAAGCAAAGGCACCT

GA
```

Example 2

Expression of Dog MCH Receptor

Measurement of MCH receptor expression in the aequorin-expressing stable reporter cell line 293-AEQ17 (Button et al., 1993, *Cell Calcium*, 14, 663–671) was performed using a Luminoskan RT luminometer (Labsystems Inc., Gaithersburg, Md.) controlled by custom software written for a Macintosh PowerPC 6100. 293-AEQ17 cells ($8 \times 10^5$ cells plated 18 hours before transfection in a T75 flask) were transfected with 22 μg of dog MCH receptor plasmid DNA: 264 μg lipofectamine.

Following approximately 40 hours of expression the apo-aequorin in the cells was charged for 4 hours with coelenterazine (10 μM) under reducing conditions (300 μM reduced glutathione) in ECB buffer (140 mM NaCl, 20 mM KCl, 20 mM HEPES-NaOH [pH=7.4], 5 mM glucose, 1 mM $MgCl_2$, 1 mM $CaCl_2$, 0.1 mg/ml bovine serum albumin). The cells were harvested, washed once in ECB medium and resuspended to 500,000 cells/ml. 100 μl of cell suspension (corresponding to $5 \times 10^4$ cells) was then injected into the test plate containing MCH, and the integrated light emission was recorded over 30 seconds, in 0.5 second units. 20 μL of lysis buffer (0.1% final Triton X-100 concentration) was then injected and the integrated light emission recorded over 10 seconds, in 0.5 second units.

The "fractional response" values for each well were calculated by taking the ratio of the integrated response to the initial challenge to the total integrated luminescence including the Triton X-100 lysis response. The $EC_{50}$ value for activation of the dog MCH receptor was ~30 nM.

Other embodiments are within the following claims. While several embodiments have been shown and described, various modifications may be made without departing from the spirit and scope of the present invention.

---

What is claimed is:

1. A purified polypeptide comprising an amino acid region of SEQ. ID. NO. 1 selected from the group consisting of:

| | |
|---|---|
| SEQ. ID. NO: 7 | LEASLLPPGP, |
| SEQ. ID. NO. 8 | SEGPDNLTSAGP, |
| SEQ. ID. NO. 9 | RRTGNVSYIN, |
| SEQ. ID. NO. 10 | PFPGGTVGCG, and |
| SEQ. ID. NO. 11 | ILQRMMSSVA. |

2. The polypeptide of claim 1, wherein said polypeptide comprises the amino acid sequence of SEQ. ID. NO. 1.

3. The polypeptide of claim 2, wherein said polypeptide consists of the amino acid sequence of SEQ. ID. NO. 1.

4. A purified nucleic acid comprising a nucleotide sequence encoding for the polypeptide of claim 1.

5. A purified nucleic acid comprising a nucleotide sequence region of SEQ. ID. NO. 4 selected from the group consisting of:

| | |
|---|---|
| SEQ. ID. NO. 12 | CCTCGGAGGGCCCGGACAACC, |
| SEQ. ID. NO. 13 | ACCTCTGCCGGGCCACCTCGT, |
| SEQ. ID. NO. 14 | GCCCTTCGTGGTCATCACAGCCGCGTAT, |
| SEQ. ID. NO. 15 | TGTCCTCGGTAGCCCCTGCCTCTCAA, and |
| SEQ. ID. NO. 16 | TTCGAGCCGTCAGCAATGCT. |

6. The purified nucleic acid of claim 5, wherein said nucleic acid comprises the nucleotide sequence of SEQ ID NO: 4.

7. The purified nucleic acid of claim 6, wherein said nucleic acid consists of the nucleotide sequence of SEQ ID NO: 4.

8. A nucleic acid comprising a recombinant nucleotide sequence encoding for a polypeptide comprising an amino acid region of SEQ. ID. NO. 1 selected from the group consisting of:

| | |
|---|---|
| SEQ. ID. NO. 7 | LEASLLPPGP, |
| SEQ. ID. NO. 8 | SEGPDNLTSAGP, |
| SEQ. ID. NO. 9 | RRTGNVSYIN, |
| SEQ. ID. NO. 10 | PFPGGTVGCG, and |
| SEQ. ID. NO. 11 | ILQRMMSSVA. |

9. The nucleic acid of claim 8, wherein said polypeptide comprises the amino acid sequence of SEQ ID NO:1.

10. The nucleic acid of claim 8, wherein said polypeptide consists of the amino acid sequence of SEQ ID NO:1.

11. The nucleic acid of claim 8, wherein said nucleic acid is an expression vector.

12. A recombinant cell comprising the expression vector of claim 11.

13. A recombinant cell made by a process comprising the step of introducing into said cell the expression vector of claim 11.

14. A method of measuring the ability of a test compound to affect MCH receptor activity comprising the steps of:
 a) contacting a recombinant cell with said compound, wherein said recombinant cell comprises a recombinant nucleic acid expressing a functional MCH receptor that comprises the amino acid sequence of SEQ. ID. NO. 1; and
 b) measuring MCH receptor activity.

15. The method of claim 14, wherein said MCH receptor consists of the sequence of SEQ. ID. NO. 1.

16. The method of claim 15, wherein said contacting further comprises contacting the cell with a MCH agonist to stimulate MCH receptor activity, and measuring the ability of said compound to modulate MCH receptor activity.

* * * * *

SEQUENCE LISTING

<160> NUMBER OF SEQ ID NOS: 18

<210> SEQ ID NO 1
<211> LENGTH: 353
<212> TYPE: PRT
<213> ORGANISM: Dog

<400> SEQUENCE: 1

Met Asp Leu Glu Ala Ser Leu Leu Pro Pro Gly Pro Asn Ala Ser Asn
  1               5                  10                  15

Thr Ser Glu Gly Pro Asp Asn Leu Thr Ser Ala Gly Pro Pro Arg Arg
             20                  25                  30

Thr Gly Asn Val Ser Tyr Ile Asn Ile Ile Met Pro Ser Val Phe Gly
         35                  40                  45

Thr Ile Cys Leu Leu Gly Ile Ile Gly Asn Ser Thr Val Ile Phe Ala
     50                  55                  60

Val Val Lys Lys Ser Lys Leu His Trp Cys Ser Asn Val Pro Asp Ile

```
                65                  70                  75                  80
            Phe Ile Ile Asn Leu Ser Val Val Asp Leu Leu Phe Leu Leu Gly Met
                            85                  90                  95
            Pro Phe Met Ile His Gln Leu Met Gly Asn Gly Val Trp His Phe Gly
                            100                 105                 110
            Glu Thr Met Cys Thr Leu Ile Thr Ala Met Asp Ala Asn Ser Gln Phe
                            115                 120                 125
            Thr Ser Thr Tyr Ile Leu Thr Ala Met Ala Ile Asp Arg Tyr Leu Ala
                        130                 135                 140
            Thr Val His Pro Ile Ser Ser Thr Lys Phe Arg Lys Pro Ser Val Ala
            145                 150                 155                 160
            Thr Leu Val Ile Cys Leu Leu Trp Ala Leu Ser Phe Ile Ser Ile Thr
                            165                 170                 175
            Pro Val Trp Leu Tyr Ala Arg Leu Ile Pro Phe Pro Gly Gly Thr Val
                            180                 185                 190
            Gly Cys Gly Ile Arg Leu Pro Asn Pro Asp Thr Asp Leu Tyr Trp Phe
                            195                 200                 205
            Thr Leu Tyr Gln Phe Phe Leu Ala Phe Ala Leu Pro Phe Val Val Ile
                        210                 215                 220
            Thr Ala Ala Tyr Val Arg Ile Leu Gln Arg Met Met Ser Ser Val Ala
            225                 230                 235                 240
            Pro Ala Ser Gln Arg Ser Ile Arg Leu Arg Thr Lys Arg Val Thr Arg
                            245                 250                 255
            Thr Ala Ile Ala Ile Cys Leu Val Phe Phe Val Cys Trp Ala Pro Tyr
                            260                 265                 270
            Tyr Val Leu Gln Leu Thr Gln Leu Ser Ile Ser Arg Pro Thr Leu Thr
                            275                 280                 285
            Phe Val Tyr Leu Tyr Asn Ala Ala Ile Ser Leu Gly Tyr Ala Asn Ser
                        290                 295                 300
            Cys Leu Asn Pro Phe Val Tyr Ile Val Leu Cys Glu Thr Phe Arg Lys
            305                 310                 315                 320
            Arg Leu Val Leu Ser Val Lys Pro Ala Ala Gln Gly Gln Leu Arg Ala
                            325                 330                 335
            Val Ser Asn Ala Gln Thr Ala Asp Glu Glu Arg Thr Glu Ser Lys Gly
                        340                 345                 350
            Thr

<210> SEQ ID NO 2
<211> LENGTH: 353
<212> TYPE: PRT
<213> ORGANISM: Human

<400> SEQUENCE: 2

Met Asp Leu Glu Ala Ser Leu Leu Pro Thr Gly Pro Asn Ala Ser Asn
            1               5                   10                  15
            Thr Ser Asp Gly Pro Asp Asn Leu Thr Ser Ala Gly Ser Pro Pro Arg
                            20                  25                  30
            Thr Gly Ser Ile Ser Tyr Ile Asn Ile Ile Met Pro Ser Val Phe Gly
                            35                  40                  45
            Thr Ile Cys Leu Leu Gly Ile Ile Gly Asn Ser Thr Val Ile Phe Ala
                        50                  55                  60
            Val Val Lys Lys Ser Lys Leu His Trp Cys Asn Asn Val Pro Asp Ile
            65                  70                  75                  80
            Phe Ile Ile Asn Leu Ser Val Val Asp Leu Leu Phe Leu Leu Gly Met
```

```
                    85                  90                  95
Pro Phe Met Ile His Gln Leu Met Gly Asn Gly Val Trp His Phe Gly
            100                 105                 110
Glu Thr Met Cys Thr Leu Ile Thr Ala Met Asp Ala Asn Ser Gln Phe
            115                 120                 125
Thr Ser Thr Tyr Ile Leu Thr Ala Met Ala Ile Asp Arg Tyr Leu Ala
            130                 135                 140
Thr Val His Pro Ile Ser Ser Thr Lys Phe Arg Lys Pro Ser Val Ala
145                 150                 155                 160
Thr Leu Val Ile Cys Leu Leu Trp Ala Leu Ser Phe Ile Ser Ile Thr
                165                 170                 175
Pro Val Trp Leu Tyr Ala Arg Leu Ile Pro Phe Pro Gly Gly Ala Val
            180                 185                 190
Gly Cys Gly Ile Arg Leu Pro Asn Pro Asp Thr Asp Leu Tyr Trp Phe
        195                 200                 205
Thr Leu Tyr Gln Phe Phe Leu Ala Phe Ala Leu Pro Phe Val Val Ile
        210                 215                 220
Thr Ala Ala Tyr Val Arg Ile Leu Gln Arg Met Thr Ser Ser Val Ala
225                 230                 235                 240
Pro Ala Ser Gln Arg Ser Ile Arg Leu Arg Thr Lys Arg Val Thr Arg
                245                 250                 255
Thr Ala Ile Ala Ile Cys Leu Val Phe Phe Val Cys Trp Ala Pro Tyr
            260                 265                 270
Tyr Val Leu Gln Leu Thr Gln Leu Ser Ile Ser Arg Pro Thr Leu Thr
            275                 280                 285
Phe Val Tyr Leu Tyr Asn Ala Ala Ile Ser Leu Gly Tyr Ala Asn Ser
            290                 295                 300
Cys Leu Asn Pro Phe Val Tyr Ile Val Leu Cys Glu Thr Phe Arg Lys
305                 310                 315                 320
Arg Leu Val Leu Ser Val Lys Pro Ala Ala Gln Gly Gln Leu Arg Ala
                325                 330                 335
Val Ser Asn Ala Gln Thr Ala Asp Glu Glu Arg Thr Glu Ser Lys Gly
            340                 345                 350
Thr

<210> SEQ ID NO 3
<211> LENGTH: 353
<212> TYPE: PRT
<213> ORGANISM: Rat

<400> SEQUENCE: 3

Met Asp Leu Gln Thr Ser Leu Leu Ser Thr Gly Pro Asn Ala Ser Asn
1               5                   10                  15
Ile Ser Asp Gly Gln Asp Asn Leu Thr Leu Pro Gly Ser Pro Pro Arg
            20                  25                  30
Thr Gly Ser Val Ser Tyr Ile Asn Ile Ile Met Pro Ser Val Phe Gly
        35                  40                  45
Thr Ile Cys Leu Leu Gly Ile Val Gly Asn Ser Thr Val Ile Phe Ala
    50                  55                  60
Val Val Lys Lys Ser Lys Leu His Trp Cys Ser Asn Val Pro Asp Ile
65                  70                  75                  80
Phe Ile Ile Asn Leu Ser Val Val Asp Leu Leu Phe Leu Leu Gly Met
                85                  90                  95
Pro Phe Met Ile His Gln Leu Met Gly Asn Gly Val Trp His Phe Gly
```

-continued

```
            100                 105                 110
    Glu Thr Met Cys Thr Leu Ile Thr Ala Met Asp Ala Asn Ser Gln Phe
                    115                 120                 125

Thr Ser Thr Tyr Ile Leu Thr Ala Met Thr Ile Asp Arg Tyr Leu Ala
                130                 135                 140

Thr Val His Pro Ile Ser Ser Thr Lys Phe Arg Lys Pro Ser Met Ala
    145                 150                 155                 160

Thr Leu Val Ile Cys Leu Leu Trp Ala Leu Ser Phe Ile Ser Ile Thr
                    165                 170                 175

Pro Val Trp Leu Tyr Ala Arg Leu Ile Pro Phe Pro Gly Gly Ala Val
                    180                 185                 190

Gly Cys Gly Ile Arg Leu Pro Asn Pro Asp Thr Asp Leu Tyr Trp Phe
                    195                 200                 205

Thr Leu Tyr Gln Phe Phe Leu Ala Phe Ala Leu Pro Phe Val Val Ile
                210                 215                 220

Thr Ala Ala Tyr Val Lys Ile Leu Gln Arg Met Thr Ser Ser Val Ala
    225                 230                 235                 240

Pro Ala Ser Gln Arg Ser Ile Arg Leu Arg Thr Lys Arg Val Thr Arg
                    245                 250                 255

Thr Ala Ile Ala Ile Cys Leu Val Phe Phe Val Cys Trp Ala Pro Tyr
                    260                 265                 270

Tyr Val Leu Gln Leu Thr Gln Leu Ser Ile Ser Arg Pro Thr Leu Thr
                    275                 280                 285

Phe Val Tyr Leu Tyr Asn Ala Ala Ile Ser Leu Gly Tyr Ala Asn Ser
                    290                 295                 300

Cys Leu Asn Pro Phe Val Tyr Ile Val Leu Cys Glu Thr Phe Arg Lys
    305                 310                 315                 320

Arg Leu Val Leu Ser Val Lys Pro Ala Ala Gln Gly Gln Leu Arg Thr
                    325                 330                 335

Val Ser Asn Ala Gln Thr Ala Asp Glu Glu Arg Thr Glu Ser Lys Gly
                340                 345                 350

Thr
```

<210> SEQ ID NO 4
<211> LENGTH: 1062
<212> TYPE: DNA
<213> ORGANISM: Artificial Sequence
<220> FEATURE:
<223> OTHER INFORMATION: Dog MCH Receptor cDNA

<400> SEQUENCE: 4

```
atggacctgg aagcctcgct gctgcccccc ggcccccaacg ccagcaacac ctcggagggc      60
ccggacaacc tcacctctgc cgggccacct cgtcgcacag ggaatgtctc ctacatcaac     120
atcatcatgc cttccgtgtt cggcaccatc tgcctgctgg gtatcatcgg gaactccaca     180
gtcatcttcg cggtggtgaa gaagtccaaa ctgcactggt gcagcaatgt ccccgacatc     240
tttatcatca acctctcggt ggtagacctc ctctttctcc tgggcatgcc cttcatgatc     300
caccagctca tgggcaatgg tgtttggcat tttggagaga ccatgtgcac actcatcacg     360
gccatggacg ccaacagtca attcaccagc acctacatcc tgaccgccat ggccattgac     420
cgctacctgg ccactgtcca ccccatctcc tccaccaagt tccggaagcc ctctgtggcc     480
accctggtga tctgcctcct atgggccctc tcattcatca gcatcacccc cgtgtggctc     540
tacgctaggc ttatccccct tccagggggc acagtgggct gtggcatccg cctgcccaac     600
```

| | |
|---|---|
| ccagacactg acctttactg gttcaccctg taccagttct tcctggcctt tgccctgccc | 660 |
| ttcgtggtca tcacagccgc gtatgtgagg atcctgcagc gcatgatgtc ctcggtagcc | 720 |
| cctgcctctc aacgcagcat ccggctgcgg acaaagaggg tgactcgcac ggccattgcc | 780 |
| atctgcctgg tcttcttcgt gtgctgggct ccctactatg tgctacagtt gacccagttg | 840 |
| tccatcagcc gcccgacact caccttttgtc tacctgtaca acgcagccat cagcttgggc | 900 |
| tatgccaaca gctgcctaaa ccccttttgtg tacatcgtgc tctgtgagac attccgcaag | 960 |
| cgcttggtcc tgtcggtgaa gcctgccgcc caggggcagc ttcgagccgt cagcaatgct | 1020 |
| cagacagctg atgaggagag gacagaaagc aaaggcacct ga | 1062 |

<210> SEQ ID NO 5
<211> LENGTH: 1062
<212> TYPE: DNA
<213> ORGANISM: Artificial Sequence
<220> FEATURE:
<223> OTHER INFORMATION: Human MCH Receptor cDNA

<400> SEQUENCE: 5

| | |
|---|---|
| atggacctgg aagcctcgct gctgcccact ggtcccaacg ccagcaacac ctctgatggc | 60 |
| cccgataacc tcacttcggc aggatcacct cctcgcacgg ggagcatctc ctacatcaac | 120 |
| atcatcatgc cttcggtgtt cggcaccatc tgcctcctgg gcatcatcgg aactccacg | 180 |
| gtcatcttcg cggtcgtgaa gaagtccaag ctgcactggt gcaacaacgt ccccgacatc | 240 |
| ttcatcatca acctctcggt agtagatctc ctctttctcc tgggcatgcc cttcatgatc | 300 |
| caccagctca tgggcaatgg ggtgtggcac tttggggaga ccatgtgcac cctcatcacg | 360 |
| gccatggatg ccaatagtca gttcaccagc acctacatcc tgaccgccat ggccattgac | 420 |
| cgctacctgg ccactgtcca ccccatctct ccacgaagt tccggaagcc ctctgtggcc | 480 |
| accctggtga tctgcctcct gtgggccctc tccttcatca gcatcacccc tgtgtggctg | 540 |
| tatgccagac tcatcccctt cccaggaggt gcagtgggct gcggcatacg cctgcccaac | 600 |
| ccagacactg acctctactg gttcaccctg taccagtttt tcctggcctt tgccctgcct | 660 |
| tttgtggtca tcacagccgc atacgtgagg atcctgcagc gcatgacgtc ctcagtggcc | 720 |
| cccgcctccc agcgcagcat ccggctgcgg acaaagaggg tgaccgcac agccatcgcc | 780 |
| atctgtctgg tcttcttttgt gtgctgggca ccctactatg tgctacagct gacccagttg | 840 |
| tccatcagcc gcccgaccct caccttttgtc tacttataca atgcggccat cagcttgggc | 900 |
| tatgccaaca gctgcctcaa ccccttttgtg tacatcgtgc tctgtgagac gttccgcaaa | 960 |
| cgcttggtcc tgtcggtgaa gcctgcagcc caggggcagc ttcgcgctgt cagcaacgct | 1020 |
| cagacggctg acgaggagag gacagaaagc aaaggcacct ga | 1062 |

<210> SEQ ID NO 6
<211> LENGTH: 1062
<212> TYPE: DNA
<213> ORGANISM: Artificial Sequence
<220> FEATURE:
<223> OTHER INFORMATION: Rat MCH Receptor cDNA

<400> SEQUENCE: 6

| | |
|---|---|
| atggatctgc aaacctcgtt gctgtccact ggccccaatg ccagcaacat ctccgatggc | 60 |
| caggataatc tcacattgcc ggggtcacct cctcgcacag ggagtgtctc ctacatcaac | 120 |
| atcattatgc cttcgtgtt tggtaccatc tgtctcctgg catcgtggg aaactccacg | 180 |
| gtcatctttg ctgtggtgaa gaagtccaag ctacactggt gcagcaacgt ccccgacatc | 240 |

```
ttcatcatca acctctctgt ggtggatctg ctcttcctgc tgggcatgcc tttcatgatc      300
caccagctca tggggaacgg cgtctggcac tttggggaaa ccatgtgcac cctcatcaca      360
gccatggacg ccaacagtca gttcactagc acctacatcc tgactgccat gaccattgac      420
cgctacttgg ccaccgtcca ccccatctcc tccaccaagt tccggaagcc ctccatggcc      480
accctggtga tctgcctcct gtgggcgctc tccttcatca gtatcacccc tgtgtggctc      540
tacgccaggc tcattccctt cccagggggt gctgtgggct gtggcatccg cctgccaaac      600
ccggacactg acctctactg gttcactctg taccagtttt tcctggcctt tgcccttccg      660
tttgtggtca ttaccgccgc atacgtgaaa atactacagc gcatgacgtc ttcggtggcc      720
ccagcctccc aacgcagcat ccggcttcgg acaaagaggg tgacccgcac ggccattgcc      780
atctgtctgg tcttctttgt gtgctgggca ccctactatg tgctgcagct gacccagctg      840
tccatcagcc gcccgaccct cacgtttgtc tacttgtaca acgcggccat cagcttgggc      900
tatgctaaca gctgcctgaa cccctttgtg tacatagtgc tctgtgagac ctttcgaaaa      960
cgcttggtgt tgtcagtgaa gcctgcagcc caggggcagc tccgcacggt cagcaacgct     1020
cagacagctg atgaggagag gacagaaagc aaaggcacct ga                        1062
```

<210> SEQ ID NO 7
<211> LENGTH: 10
<212> TYPE: PRT
<213> ORGANISM: Artificial Sequence
<220> FEATURE:
<223> OTHER INFORMATION: Corresponds to a dog MCH receptor region

<400> SEQUENCE: 7

Leu Glu Ala Ser Leu Leu Pro Pro Gly Pro
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Corresponds to a dog MCH receptor region

<400> SEQUENCE: 8

Ser Glu Gly Pro Asp Asn Leu Thr Ser Ala Gly Pro
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Corresponds to a dog MCH receptor region

<400> SEQUENCE: 9

Arg Arg Thr Gly Asn Val Ser Tyr Ile Asn
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Corresponds to a dog MCH receptor region

<400> SEQUENCE: 10

Pro Phe Pro Gly Gly Thr Val Gly Cys Gly

<210> SEQ ID NO 11
<211> LENGTH: 10
<212> TYPE: PRT
<213> ORGANISM: Artificial Sequence
<220> FEATURE:
<223> OTHER INFORMATION: Corresponds to a dog MCH receptor region

<400> SEQUENCE: 11

Ile Leu Gln Arg Met Met Ser Ser Val Ala
1               5                   10

<210> SEQ ID NO 12
<211> LENGTH: 21
<212> TYPE: DNA
<213> ORGANISM: Artificial Sequence
<220> FEATURE:
<223> OTHER INFORMATION: Corresponds to a dog MCH receptor cDNA region

<400> SEQUENCE: 12
cctcggaggg cccggacaac c                                        21

<210> SEQ ID NO 13
<211> LENGTH: 21
<212> TYPE: DNA
<213> ORGANISM: Artificial Sequence
<220> FEATURE:
<223> OTHER INFORMATION: Corresponds to a dog MCH receptor cDNA region

<400> SEQUENCE: 13
acctctgccg ggccacctcg t                                        21

<210> SEQ ID NO 14
<211> LENGTH: 28
<212> TYPE: DNA
<213> ORGANISM: Artificial Sequence
<220> FEATURE:
<223> OTHER INFORMATION: Corresponds to a dog MCH receptor cDNA region

<400> SEQUENCE: 14
gcccttcgtg gtcatcacag ccgcgtat                                 28

<210> SEQ ID NO 15
<211> LENGTH: 26
<212> TYPE: DNA
<213> ORGANISM: Artificial Sequence
<220> FEATURE:
<223> OTHER INFORMATION: Corresponds to a dog MCH receptor cDNA region

<400> SEQUENCE: 15
tgtcctcggt agcccctgcc tctcaa                                   26

<210> SEQ ID NO 16
<211> LENGTH: 20
<212> TYPE: DNA
<213> ORGANISM: Artificial Sequence
<220> FEATURE:
<223> OTHER INFORMATION: Corresponds to a dog MCH receptor cDNA region

<400> SEQUENCE: 16
ttcgagccgt cagcaatgct                                          20

<210> SEQ ID NO 17
<211> LENGTH: 9
<212> TYPE: DNA

```
<213> ORGANISM: Artificial Sequence
<220> FEATURE:
<223> OTHER INFORMATION: PCR primer

<400> SEQUENCE: 17 atggacctg                                                           9

<210> SEQ ID NO 18
<211> LENGTH: 6
<212> TYPE: PRT
<213> ORGANISM: Artificial Sequence
<220> FEATURE:
<223> OTHER INFORMATION: MCH Receptor Segment

<400> SEQUENCE: 18

Asp Leu Glu Ala Ser Leu
 1               5
```